United States Patent [19]

Enoki et al.

[11] 4,012,451
[45] Mar. 15, 1977

[54] PROCESS FOR THE SEPARATION OF 4,4'-DICHLORODIPHENYLSULFONE

[75] Inventors: Kichiji Enoki; Takeo Fukui; Takeo Yamamoto; Toshirou Okada; Yoshiaki Miyazaki, all of Takaoka, Japan

[73] Assignee: Nippon Soda Company Limited, Tokyo, Japan

[22] Filed: Jan. 19, 1976

[21] Appl. No.: 650,158

[30] Foreign Application Priority Data

Jan. 31, 1975 Japan .............................. 50-12433

[52] U.S. Cl. .................... 260/607 AR; 260/459 R
[51] Int. Cl.² ...................................... C07C 147/06
[58] Field of Search ........................... 260/607 AR

[56] References Cited

UNITED STATES PATENTS

| | | | |
|---|---|---|---|
| 2,224,964 | 12/1940 | Huismann et al. | 260/607 AR |
| 3,334,146 | 8/1967 | Pitts et al. | 260/607 AR |
| 3,402,204 | 9/1968 | Plummer et al. | 260/607 AR |
| 3,673,259 | 6/1972 | Rosin | 260/607 AR |

Primary Examiner—Lewis Gotts
Assistant Examiner—D. R. Phillips
Attorney, Agent, or Firm—George B. Oujevolk

[57] ABSTRACT

Pure 4,4'-dichlorodiphenylsulfone is separated from the reaction mixture containing 4,4'-dichlorodiphenylsulfone and the isomers thereof by adding the reaction mixture to the mixture of trichloroethylene or tetrachloroethylene, and water to extract 4,4'-dichlorodiphenylsulfone with said organic solvent and cooling the organic solution separated from the water layer to precipitate pure 4,4'-dichlorodiphenylsulfone.

11 Claims, No Drawings

PROCESS FOR THE SEPARATION OF 4,4'-DICHLORODIPHENYLSULFONE

BACKGROUND OF THE INVENTION:

This invention relates to a new process for separating pure 4,4'-dichlorodiphenylsulfone from the reaction mixture containing 4,4'-dichlorodiphenylsulfone and the isomers thereof, namely 2,4'-isomer and 3,4'-isomer.

The 4,4'-dichlorodiphenylsulfone is useful as intermediates for medicines and synthetic resines.

Some processes for the production of 4,4'-dichlorodiphenylsulfone are known, for example, by the reaction of monochlorobenzene with dimethyl pyrosulfate and sulfuric anhydride, by the reaction of p-chlorobenzenesulfonic acid and monochlorobenzene in sulfuric acid, and by the reaction of p-chlorobenzenesulfonyl chloride and monochlorobenzene in the presence of ferric chloride as a catalyst.

Japanese Patent Publication No. 11,817/1962 and U.S. Pat. No. 3,309,409 disclose the process for the separation of the product by adding a reaction mixture to water or aqueous alkali to precipitate the product. In this method, when adding the reaction mixture containing a large amount of acidic materials to water, the precipitate of the product is contaminated by the acidic materials, the isomers (2,4'-, 3,4'-) and other impurities.

U.S. Pat. No. 3,415,887 discloses the process for the separation of the product by dissolving a reaction mixture in methylene chloride, neutralizing acidic materials by aqueous alkali, and then evaporating the separated methylene chloride solution to dryness. Also in this method, the contamination of the product by the isomers is not avoidable because the solubility of the product to methylene chloride is extremely high and the product is necessarily obtained as evaporation residue.

In the process of U.S. Pat. No. 3,334,146, the reaction mixture is dissolved in monochlorobenzene and the solution is washed with water. The solution is cooled to precipitate the product. In this method, considerably pure product is obtained, however the precipitation yield is low and the recovery of the product from the mother liquor is complicated.

The inventors have found that trichloroethylene and tetrachloroethylene are the most advantageous solvents for extraction and recrystallization of 4,4'-dichlorodiphenylsulfone, and have accomplished an industrially advantageous process for the separation of 4,4'-dichlorodiphenylsulfone.

It is the object of this invention to provide an industrially advantageous process for separating highly pure 4,4'-dichlorodiphenylsulfone from the reaction mixture which contains 2,4'-isomer and/or 3,4'-isomer as by-products.

Other and further objects, features and advantages will appear more fully from the following discription.

DETAILED DESCRIPTION OF THE INVENTION

In this invention, trichloroethylene and/or tetrachloroethylene, and water are mixed with the reaction mixture containing 4,4'-dichlorodiphenylsulfone as a main product and the isomers thereof (2,4'-and/or 3,4'-) at a desired temperature to extract 4,4'-dichlorodiphenylsulfone with said organic solvent and to remove water-soluble materials with water, and then the organic solvent layer separated from the water layer is cooled to precipitate pure 4,4'-dichlorodiphenylsulfone.

The process of the invention is applicable to all kind of the reaction mixture which are prepared by the conventional processes and contain 2,4'-isomer and/or 3,4'-isomer as impurity, and is also applicable to the crude 4,4'-dichlorodiphenylsulfone separated from the reaction mixture by the conventional methods. Namely, the terms "reaction mixture" also includes said crude product.

The amount of water varies with the extraction temperature. The required amount of water is at least the amount in which impurities soluble in water can be completely dissolved. Used amount of water may be arranged from the industrial viewpoint.

In case that sulfuric acid is contained in the reaction mixture, the concentration of aqueous sulfuric acid is adjusted to below 50% by weight, preferably 10 to 40%. When the concentration is 50% or higher, the recovery of the product decreases due to the increase of solubility of the product in aqueous sulfuric acid.

Before the separation of the organic solvent layer from the water layer, the acidic materials may be neutralized, unless a material which is precipitated in neutral or alkaline solution is contained in the reaction mixture, for example, ferric chloride used as a catalyst. Alkali metal hydroxides or carbonates are preferable for the neutralization. In this case, the required amount of water is at least the amount in which the salt formed by the neutralization can be completely dissolved.

The amount of the organic solvent varies with the extraction temperature. The required amount of the organic solvent is at least the amount in which 4,4'-dichlorodiphenylsulfone can be completely dissolved at the extraction temperature. The industrially preferable amount of the organic solvent is such amount that 4,4'-dichlorodiphenylsulfone can be dissolved at a temperature of about 10° to 20° C lower than the extraction temperature in order to prevent the precipitation of the product during the treatment due to fluctuations in temperature. It is generally 2 to 6 times 4,4'-dichlorodiphenylsulfone by weight.

In short, the reaction mixture is dissolved in trichloroethylene or tetrachloroethylene and the solution is washed with water to remove water-soluble materials.

The organic solvent layer separated from the water layer may be repeatedly washed with water at above-mentioned temperature in order to completely remove water-soluble impurities.

The solubility of 4,4'-dichlorodiphenylsulfone is shown in Table 1. The solubility in monochlorobenzene is shown for reference.

Table 1

| Solvent | Temperature (° C) | | | | | |
|---|---|---|---|---|---|---|
|  | 10 | 20 | 40 | 60 | 80 | 100 |
| trichloroethylene | 2.0 | 10.3 | 13.2 | 27.0 | 48.0 |  |
| tetrachloroethylene |  | 0.8 | 3.4 | 8.0 | 20.0 | 59.0 |
| monochlorobenzene | 8.0 | 12.0 | 21.5 | 40.8 | 80.5 |  |

(Table 1 shows gram of 4,4'-dichlorodiphenylsulfone soluble in 100 gram of solvent.)

The temperature for the extraction and the washing is a boiling point of the mixture resulting from the mixing of the reaction mixture, the organic solvent and water, or below the boiling point, and is related to the amount of organic solvent. An azeotropic point of the organic solvent and water is about 74° C in case of trichloroethylene, and about 88° C in case of tetrachloroethylene. In order to reduce the amount of the organic solvent, higher temperature is better. It is generally 40° C to a boiling point, preferably 60° C to a boiling point. Even if lower temperature is applied and a large amount of the organic solvent is used, the precipitation yield can be kept high, because the solubility is very small below 10° C. The mixture of reaction mixture, organic solvent and water should be maintained at a contemplated temperature, however, each of them may be heated before mixing or after mixing.

The time for maintaining at a contemprated temperature is not critical so long as the reaction mixture can be dissolved in the organic solvent and water. It is sufficient to maintain for about 30 minutes.

The cooling temperature is generally below 10° C, though it is not critical. The temperature of about 0° C is preferable in order to attain a high precipitation yield because the solubility of 4,4'-dichlorodiphenylsulfone is almost zero at about 0° C.

Filtered precipitate has a purity of about 99.5% or more. The precipitate can be easily purified to a purity of 99.8% or more by washing it with the used organic solvent which of amount is about 0.5 to 1 of the precipitate by volume.

The filtrate which includes mother liquor resulting from the precipitation step and washings, still contains a small amount of the product together with the isomers. The 4,4'-dichlorodiphenylsulfone contained in the filtrate is recovered by concentrating the filtrate and cooling to precipitate it. The crude product recovered from the filtrate can be easily purified as a purity of more than 99% by the recrystallization thereof from trichloroethylene or tetrachloroethylene. This means that the organic solvents used in the invention are also very advantageous recrystallization solvent.

In other words, in case that the reaction mixture does not contain water-soluble impurities, water is not necessary.

As aforementioned, this invention is applicable to the reaction mixture prepared by the reaction of monochlorobenzene with dimethyl pyrosulfate and sulfuric anhydride. Said reaction mixture contains a large amount of methyl hydrogensulfate as a by-product.

The inventors have found that distillation of said reaction mixture under reduced pressure attains the recovery of methyl hydrogensulfate as dimethyl sulfate.

On the occasion of the distillation of said reaction mixture under reduced pressure, the methyl hydrogensulfate changes into dimethyl sulfate and the dimethyl sulfate is distilled out without any unfavorable influence on 4,4'-dichlorodiphenylsulfone. Said recovery of methyl hydrogensulfate as dimethyl sulfate is carried out according to the following reaction equation.

$$2CH_3SO_4H \rightleftarrows (CH_3)_2SO_4 + H_2SO_4$$

The distillation operation is easily carried out because the mutual solubility of 4,4'-dichlorodiphenylsulfone and, methyl hydrogensulfate or sulfuric acid, is enough high throughout the distillation. In addition, 4,4'-dichlorodiphenylsulfone do not cause any side reaction at the following temperature range throughout the distillation.

The temperature range of 100° to 200° C is applicable to the recovery of dimethyl sulfate by distillation. It is preferably 110° to 160° C. The temperature means a still temperature. The temperature lower than 100° C makes the recovery of dimethyl sulfate low and the temperature higher than 200° C causes a side reaction of 4,4'-dichlorodiphenylsulfone.

The pressure for the distillation may be 50 mmHg or lower. The pressure of 2 to 20 mmHg is industrially preferable.

An amount of 70 to 90% of methyl hydrogensulfate contained in the reaction mixture is recovered as dimethyl sulfate by a batchwise distillation of the reaction mixture under the above-mentioned conditions.

The recovered dimethyl sulfate is available for the production of 4,4'-dichlorodiphenylsulfone.

Therefore, in case of applying this invention to the reaction mixture prepared by the reaction of monochlorobenzene with dimethy pyrosulfate and sulfuric anhydride, it is preferable to conduct the above-mentioned distillation before extraction.

According to this invention, highly pure 4,4'-dichlorodiphenylsulfone is easily obtained by an industrially advantageous process.

To further illustrate this invention, and not by way of limitation, the following examples are given.

PREPARATION OF THE REACTION MIXTURE

In a reactor was placed 630 g of dimethyl sulfate, and 800 g of sulfuric anhydride was dropped into it while maintaning the reaction solution at 70°–75° C. After adding sulfuric anhydride, the reaction solution was maintained for 30 minutes at said temperature to prepare the mixed solution of dimethyl pyrosulfate and sulfuric anhydride.

In another reactor was placed 1125 g of monochlorobenzene, and said mixed solution of dimethyl pyrosulfate and sulfuric anhydride was added to it in about 1 hour at 50°–55° C. The reaction solution was maintained for 1 hour at said temperature, and then heated to elevate the temperature gradually to 80° C and maintained at 80° C for 15 minutes. Thus, the prepared reaction solution was 2550g weight.

COMPARATIVE EXAMPLE

In 600 ml of cold water was poured 510 g of the above-mentioned reaction solution to precipitate 4,4'-dichlorodiphenylsulfone and extract the acidic materials. The precipitated crystal was repeatedly washed with boiling water until the pH of the filtrate came to 5, and dried to obtain 254.5 g of amorphous crystal of the product. The yield was 88.7% to the monochlorobenzene. As the result of the analysis by gaschromatography, it was identified that the product was composed of 93.9% of 4,4'-dichlorodiphenylsulfone, 0.7% of 3,4'-isomer and 5.8% of 2,4'-isomer.

The yield of 4,4'-dichlorodiphenylsulfone is 83.3% to monochlorobenzene.

EXAMPLE 1

In the mixture of 500 ml of water and 600 g of trichloroethylene maintained at about 60° C was poured 510 g of the aforementioned reaction solution under stirring, and then 400 ml of 30% aqueous caustic soda was added to the mixture to neutralize the acidic substances. On the occasion of the neutralization, the temperature of the mixture was elevated to the azeotropic point of water and trichloroethylene. Said addition of caustic soda was carried out under reflux.

After the addition of caustic soda, the mixture was stirred for 30 minutes, and the organic solvent layer was separated from the water layer. The organic solution was cooled to 0° C to precipitate the product. The precipitated crystal was filtrated and dried to obtain 222.3 g of white needles (yield: 77.5% to monochlorobenzene). The filtrate was concentrated to about 80 ml and cooled to obtain 18.2 g of crude crystal of the product (yield: 6.3% to monochlorobenzene). The crude crystal was recrystallized from 40 ml trichloroethylene to obtain 12.6g of white needles (yield: 4.4% to monochlorobenzene).

Each crystal was analyzed by gaschromatography. The result was shown in Table 2.

Table 2

| Crystal | Yield (%) | Composition 4.4'- | 3.4'- | 2.4'- |
|---|---|---|---|---|
| I | 77.5 | 99.6 | | 0.36 |
| II | 6.3 | 90.5 | 1.60 | 7.80 |
| III | 4.4 | 99.5 | | 0.40 |
| IV (I + III) | 81.9 | 99.6 | | 0.36 |

I: first precipitated crystal
II: crude crystal
III: purified crystal of crystal II

EXAMPLE 2

In an oil bath maintained at 140°–150° C was distilled at 5 mmHg 510 g of the reaction solution obtained in the above-mentioned "Preparation of the Reaction mixture" to recover 114 g of methyl hydrogensulfate.

The residual solution was treated as in Example 1. The result was shown in Table 3.

Table 3

| Crystal | Yield (%) | Composition 4.4'- | 3.4'- | 2.4'- |
|---|---|---|---|---|
| I | 73.7 | 99.7 | | 0.25 |
| II | 9.72 | 91.2 | 0.99 | 7.82 |
| III | 7.77 | 99.65 | | 0.31 |
| IV (I + III) | 81.4 | 99.7 | | 0.25 |

I: first precipitated crystal
II: crude crystal
III: purified crystal of crystal II

EXAMPLE 3

The residual solution of distillation was prepared as in Example 2 and was added to the mixture of 150 ml of water and 810 g of tetrachloroethylene. The mixture was maintained at 85° to 95° C for 30 minutes with stirring. The organic solvent layer was separated from the water layer and was twice washed with water as above.

The tetrachloroethylene solution was cooled to 0° C to precipitate 4,4'-dichlorodiphenylsulfone and the precipitated product was washed with 160 g of tetrachloroethylene at 20° C. Drying of the precipitate gave 228.5 g of white needles.

The mother liquor of the precipitation and the washings of the precipitate were concentrated and cooled to precipitate a crude product. The crude product was recrystallized from tetrachloroethylene to obtain a purified white needles.

Each crystal was analyzed by gaschromatography and the result was shown in Table 4.

Table 4

| Crystal | Yield g. | % | Composition 4.4'- | 3.4'- | 2.4'- |
|---|---|---|---|---|---|
| I | 228.5 | 79.62 | 99.8 | — | 0.20 |
| II | 3.7 | 0.78 | 83.0 | 1.73 | 15.25 |
| III | 7.0 | 2.44 | 72.0 | 1.64 | 26.32 |
| IV | 7.0 | 2.44 | 99.8 | — | 0.20 |
| V (I + IV) | 235.5 | 82.06 | 99.8 | — | 0.20 |

I: first precipitated crystal
II: crude crystal from washings
III: crude crystal from mother liquor
IV: purified crystal of II + III

EXAMPLE 4

The separation of 4,4'-dichlorodiphenylsulfone was carried out as in Example 3 except that the organic solvent was trichloroethylene and the temperature was 75° to 85° C.

The result was shown in Table 5.

Table 5

| Crystal | Yield g. | % | Composition 4.4'- | 3.4'- | 2.4'- |
|---|---|---|---|---|---|
| I | 208.5 | 72.65 | 99.8 | — | 0.18 |
| II | 7.0 | 2.44 | 89.4 | 1.88 | 8.77 |
| III | 22.1 | 7.70 | 90.9 | 1.67 | 7.43 |
| IV | 24.0 | 8.36 | 99.8 | — | 0.23 |
| V (I + IV) | 232.5 | 80.01 | 99.8 | — | 0.18 |

I: first precipitated crystal
II: crude crystal from washings
III: crude crystal from mother liquor
IV: purified crystal of II + III

We claim:

1. A process for the separation of 4,4'-dichlorodiphenylsulfone from a reaction mixture containing said 4,4'-dichlorodiphenylsulfone and its isomers which comprises dissolving the reaction mixture in an organic solvent selected from the group consisting of trichloroethylene, tetrachloroethylene and mixture thereof and cooling the organic solution to precipitate 4,4'-dichlorodiphenylsulfone.

2. A process according to claim 1 wherein said organic solution is washed with water before the cooling.

3. A process according to claim 1 wherein the amount of organic solvent is in the range of 2 to 6 times weight of 4,4'-dichlorodiphenylsulfone contained in the reaction mixture.

4. A process according to claim 1 wherein 4,4'-dichlorodiphenylsulfone contained in the mother liquor of the precipitation is recovered.

5. A process according to claim 4 wherein said recovered 4,4'-dichlorodiphenylsulfone is purified by recrystallization from said organic solvent.

6. A process for the separation of 4,4'-dichlorodiphenylsulfone from a reaction mixture containing 2,4'-; 3,4'-and/or 4,4'-dichlorodiphenylsulfone and sulfuric acid which comprises mixing the reaction mixture with water and at least one organic solvent selected from the group consisting of trichloroethylene and tetrachloroethylene, the amount of said organic solvent is in the range of 2 to 6 times weight of 4,4'-dichlorodiphenylsulfone contained in the reaction mixture and the concentration of aqueous sulfuric acid resulting from said mixing of the reaction mixture, water and organic solvent is below 50% by weight, and cooling the organic solution separated from the aqueous solution to precipitate 4,4'-dichlorodiphenylsulfone.

7. A process according to claim 6 wherein said concentration of aqueous solfuric acid is in the range of 10 to 40% by weight.

8. A process for the selective separation of 4,4'-dichlorodiphenylsulfone from a reaction mixture which includes its isomers and which is prepared by the reaction of monochlorobenzene with dimethyl pyrosulfate and sulfuric anhydride which comprises recovering dimethyl sulfate from the reaction mixture by distillation at the pressure of 50 mmHg or less, mixing the residue of the distillation with water and at least one organic solvent selected from the group consisting of trichloroethylene and tetrachloroethylene, and cooling the organic solution separated from the aqueous solution to selectively precipitate 4,4'-dichlorodiphenylsulfone.

9. A process according to claim 8 wherein the amount of organic solvent is in the range of 2 to 6 times weight of 4,4'-dichlorodiphenylsulfone contained in the reaction mixture.

10. A process according to claim 8 wherein the concentration of aqueous sulfuric acid resulting from said mixing of the residue of the distillation, water and organic solvent is below 50% by weight.

11. A process according to claim 10 wherein said concentration of aqueous sulfuric acid is in the range of 10 to 40% by weight.

* * * * *